(12) United States Patent
Walker et al.

(10) Patent No.: US 6,566,066 B1
(45) Date of Patent: May 20, 2003

(54) AQUAPORIN-8 VARIANT

(75) Inventors: Michael G. Walker, Sunnyvale, CA (US); Wayne Volkmuth, Calabasas, CA (US); Tod M. Klinger, San Carlos, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/610,906

(22) Filed: Jul. 6, 2000

Related U.S. Application Data

(63) Continuation-in-part of application No. 09/226,994, filed on Jan. 7, 1999, now abandoned.

(51) Int. Cl.[7] .................................................. C12Q 1/68
(52) U.S. Cl. ........................ 435/6; 435/69.1; 435/252.3; 435/320.1; 536/23.5; 536/24.3
(58) Field of Search .......................... 435/6, 320.1, 325, 435/435, 69.1, 252.3; 536/27.1, 23.5, 24.31; 514/44

(56) References Cited

PUBLICATIONS

Tani et al (GenBank Accession No. AF 067797, Released Dec. 1, 1999).*
Ishibashi et al (Biochem. Biophys. Res. Comm. 237: 714 (1997).*
Koyama et al (Genomics 54: 169 (1998).*
Lockhart et al (Nature Biotechnology 14: 1675 (1996).*
Koyama, Y. et al., "Molecular Cloning of a New Aquaporin from Rat Pancreas and Liver", *J. Biol. Chem.* 272 (48): 30329–30333 (1997).
Bolton, A.E. and Hunter, W.M., "The Labelling of Proteins to High Specific Radioactivities by Conjugation to a [125]I–Containing Acylating Agent", *Biochem. J.* 133: 529–539 (1973).

* cited by examiner

*Primary Examiner*—James Martinell
(74) *Attorney, Agent, or Firm*—Incyte Genomics, Inc.

(57) ABSTRACT

The invention provides a mammalian cDNA which encodes a mammalian AQP8V. It also provides for the use of the cDNA, fragments, complements, and variants thereof and of the encoded protein, portions thereof and antibodies thereto for diagnosis and treatment of pancreatic disorders, particularly type I diabetes. The invention additionally provides expression vectors and host cells for the production of the protein and a transgenic model system.

13 Claims, 7 Drawing Sheets

```
                  9          18         27         36         45         54
5' GGT GAG CCC TCT GTC GGC ATC TTC CTC TCC AGG CTG GCA GAG CAA GGG GGG CTG
   Gly Glu Pro Ser Val Gly Ile Phe Leu Ser Arg Leu Ala Glu Gln Gly Gly Leu 63         72         81         90         99        108
   TGA ATT AAT TCA AGG TTG GGG GTC GGG GCC TTC TAT ATC TGG ACT TGC CTC CCA
   *** Ile Asn Ser Arg Leu Gly Val Gly Ala Phe Tyr Ile Trp Thr Cys Leu Pro 117        126        135        144        153        162
   CCC GTG TCC TCT GTC CCT TTT TCC CTA CGG CAG ATA GCC ATG TGT GAG CCT GAA
   Pro Val Ser Ser Val Pro Phe Ser Leu Arg Gln Ile Ala Met Cys Glu Pro Glu 171        180        189        198        207        216
   TTT GGC AAT GAC AAG GCC AGG GAG AGC GTG GGT GGC AGG GTG TGG CGA GTG TCC
   Phe Gly Asn Asp Lys Ala Arg Glu Ser Val Gly Gly Arg Val Trp Arg Val Ser 225        234        243        252        261        270
   TGG TAC GAA CGG TTT GTG CAG CCA TGT CTG GTC GAA CTG CTG GGC TCT GCT CTC
   Trp Tyr Glu Arg Phe Val Gln Pro Cys Leu Val Glu Leu Leu Gly Ser Ala Leu 279        288        297        306        315        324
   TTC ATC TTC ATC GGG TGC CTG TCG GTC ATT GAG AAT GGG GAC ACT GGG GGG CTG
   Phe Ile Phe Ile Gly Cys Leu Ser Val Ile Glu Asn Gly Asp Thr Gly Gly Leu 333        342        351        360        369        378
   CTG CAG CCG GCC CTG GCT TTG GGG CTC GTG ATT GCC ACG CTG
   Leu Gln Pro Ala Leu Ala His Gly Leu Leu Ala Leu Gly Leu Val Ile Ala Thr Leu
```

Figure 1A

```
           387       396       405       414       423       432
       GGG AAT ATC AGT GGT GGA CAC TTC AAC CCT GCG GTG TCC CTG GCA GCC ATG CTG
       Gly Asn Ile Ser Gly Gly His Phe Asn Pro Ala Val Ser Leu Ala Ala Met Leu 441       450       459       468       477       486
       ATC GGA GGC CTC AAC CTG GTG ATG CTC CTC CCG TAC TGG GTC TCA CAG CTG CTC
       Ile Gly Gly Leu Asn Leu Val Met Leu Leu Pro Tyr Trp Val Ser Gln Leu Leu 495       504       513       522       531       540
       GGG GGG ATG CTC GGG GCT GCC TTG GCC AAG GCG GTG AGT CCT GAG GAG AGG TTC
       Gly Gly Met Leu Gly Ala Ala Leu Ala Lys Ala Val Ser Pro Glu Glu Arg Phe 549       558       567       576       585       594
       TGG AAT GCA TCT GGG GCG GCC TTT GTG ACA GTC CAG GAG CAG CAG GTG GCA
       Trp Asn Ala Ser Gly Ala Ala Phe Val Thr Val Gln Glu Gln Gln Val Ala 603       612       621       630       639       648
       GGG GCG TTG GTG GCA GAG ATC ATC CTG ACG ACG CTG GCC CTG GCT GTA TGC
       Gly Ala Leu Val Ala Glu Ile Ile Leu Thr Thr Leu Ala Leu Ala Val Cys 657       666       675       684       693       702
       ATG GCC ATC AAT GAG AAG ACA AAG GGC CCT CTG GCC CCG TTC TCC ATC GGC
       Met Gly Ala Ile Asn Glu Lys Thr Lys Gly Pro Leu Ala Pro Phe Ser Ile Gly 711       720       729       738       747       756
       TTT GCC GTC ACC GAT ATC CTG GCT GGG GGC CCT GTG TCT GGA GGC TGC ATG
       Phe Ala Val Thr Val Asp Ile Leu Ala Gly Gly Pro Val Ser Gly Gly Cys Met
```

Figure 1B

```
765                  774                  783
AAT CCC GCC CGT GCT TTT GGA CCT GCG GTG GCC AAC CAC TGG AAC TTC CAC
Asn Pro Ala Arg Ala Phe Gly Pro Ala Val Val Ala Asn His Trp Asn Phe His 819                  828                  837                  846                  855
TGG ATC TAC TGG CTG GGC CCA CTC CTG GCT GGC CTG CTT GTT GGA CTG CTC ATT
Trp Ile Tyr Trp Leu Gly Pro Leu Leu Ala Gly Leu Leu Val Gly Leu Leu Ile 873                  882                  891                  900                  909                  918
AGG TGC TTC ATT GGA GAT GGG AAG ACC CGC CTC ATC CTG AAG GCT CGG TGA AGC
Arg Cys Phe Ile Gly Asp Gly Lys Thr Arg Leu Ile Leu Lys Ala Arg *

927                  936                  945                  954                  963                  972
AGA GCT CGT GGG ATT CCT GCT GCT CCA GGT GTC CTC AGC TCA CCT GTC CCA GAC 981                  990                  999                  1008                 1017                 1026
TGA GGA CAG GGG AGT TCC TGC ATT TCC TGC CG GGC AGA GGC CCA GAG GAG CGA 1035                 1044                 1053                 1062                 1071                 1080
CCC CCT GCT TCC ACT GCT CGT TGG GCC TGC TTT CTC AGA TAG ACT GAC TGC TGA GGA 1089                 1098                 1107                 1116                 1125                 1134
GGC TCT AGG TTC TTG GAA TTC CTT TGT GCT CAT CAG AGA CCC CAG CCT GGG GAA 1143                 1152                 1161                 1170                 1179                 1188
CAC GCT GCC CGC ACT GCC CAG AGA GCA GTG CAA GTG CAA ACA CCA CAA CAC GAG CGT GTT
His Ala Ala Arg Thr Ala Gln Arg Ala Val Gln Thr Pro Gln His Glu Arg Val
```

Figure 1C

```
              1197        1206        1215        1224        1233        1242
         TCT TGA GAG GAA TGT CCC CGA GTT GGA CAA GGA GGC TGT TTC TGC ACA TCA GCT 1251        1260        1269        1278        1287        1296
         CAT TTC CCG CAC CCC ATT TCT TGC TTG ATT GCT TTG GGG GCC TGG CCA CTT
         His Phe Pro His Pro Ile Ser Cys Leu Ile Ala Leu Leu Gly Ala Trp Pro Leu 1305        1314        1323        1332        1341        1350
         CCT TGC TTC TCA AGC TGA CAA TTC TCA CTT TGC AAT AAA TAG TCC AGT GTT TCC

TTC C 3'
```

Found in:

| Library ID | Clone Count | Library Description | Abs Abund | Percent Abund | Percent Spec |
|---|---|---|---|---|---|
| PANCDIT01 | 1807 | pancreas, type I diabetes, 15M | 1 | 0.0553 | 2.44 |
| PANCNOT23 | 3920 | pancreas, type I diabetes, 43F | 2 | 0.0510 | 2.28 |
| PANCNOT01 | 4485 | pancreas, 29M | 2 | 0.0446 | 2.00 |
| PANCNOT15 | 3646 | pancreas, islet cell hyperplasia, 15M | 1 | 0.0274 | 1.23 |
| PANCNOT21 | 3846 | pancreas, 8M | 1 | 0.0260 | 1.16 |
| PANCNOT17 | 4037 | pancreas, mw/neuroendocrine CA, aw/node, liver mets, 65F | | | |
| PANCNOT05 | 6805 | pancreas, 2M | 1 | 0.0248 | 1.11 |
| ISLTNOT01 | 15551 | pancreas, islet cells, pool | 1 | 0.0147 | 0.66 |
| | | | 2 | 0.0129 | 0.58 |

Not found in:

| Library ID | Clone Count | Library Description |
|---|---|---|
| PANCDIT03 | 697 | pancreas, type II diabetes, 57M |
| PANCNOP03 | 590 | pancreas, 34F, WN |
| PANCNOT07 | 7006 | pancreas, fetal, 23wM |
| PANCNOT08 | 3906 | pancreas, pancreatitis, mw/adenoCA, 65F, m/PANCTUT01 |
| PANCNOT16 | 2812 | pancreas, aw/Patau's, fetal, 20wM |
| PANCNOT19 | 3775 | pancreas, 8M |
| PANCNOT22 | 1357 | pancreas, 17F |
| PANCTUM01 | 3427 | pancreatic tumor line, adenoCA, untreated, WM/WN |
| PANCTUP01 | 1205 | pancreatic tumor, TIGR |
| PANCTUP02 | 1416 | pancreatic tumor, TIGR |
| PANCTUP03 | 19177 | pancreas tumor, adenoCA, 3' CGAP |
| PANCTUT01 | 3873 | pancreatic tumor, adenoCA, 65F, m/PANCNOT08 |
| PANCTUT02 | 11565 | pancreatic tumor, anaplastic CA, 45F |
| PANCISM01 | 1195 | pancreas, islet cells, WM |

Figure 3

Human 2774542CD1
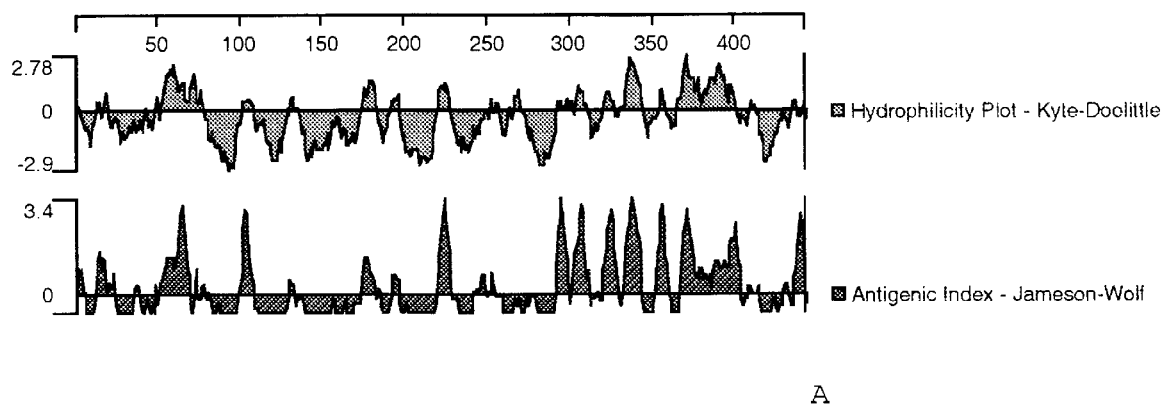
A
Rat g2346968
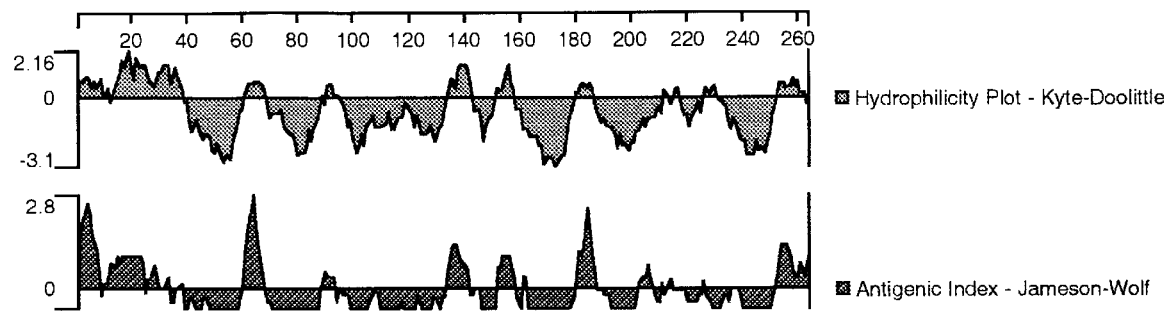
B
Figure 4

SEQUENCE LISTING

<160> NUMBER OF SEQ ID NOS: 12

<210> SEQ ID NO 1
<211> LENGTH: 443
<212> TYPE: PRT
<213> ORGANISM: Homo sapiens
<220> FEATURE:
<221> NAME/KEY: misc_feature
<223> OTHER INFORMATION: Incyte ID No: 2774542CD1

<400> SEQUENCE: 1

```
Gly Glu Pro Ser Val Gly Ile Phe Leu Ser Arg Leu Ala Glu Gln
 1               5                  10                  15

Gly Gly Leu Ile Asn Ser Arg Leu Gly Val Gly Ala Phe Tyr Ile
                20                  25                  30

Trp Thr Cys Leu Pro Pro Val Ser Ser Val Pro Phe Ser Leu Arg
                35                  40                  45

Gln Ile Ala Met Cys Glu Pro Glu Phe Gly Asn Asp Lys Ala Arg
                50                  55                  60

Glu Pro Ser Val Gly Gly Arg Trp Arg Val Ser Trp Tyr Glu Arg
                65                  70                  75

Phe Val Gln Pro Cys Leu Val Glu Leu Leu Gly Ser Ala Leu Phe
                80                  85                  90

Ile Phe Ile Gly Cys Leu Ser Val Ile Glu Asn Gly Thr Asp Thr
                95                  100                 105

Gly Leu Leu Gln Pro Ala Leu Ala His Gly Leu Ala Leu Gly Leu
                110                 115                 120

Val Ile Ala Thr Leu Gly Asn Ile Ser Gly Gly His Phe Asn Pro
                125                 130                 135

Ala Val Ser Leu Ala Ala Met Leu Ile Gly Gly Leu Asn Leu Val
                140                 145                 150

Met Leu Leu Pro Tyr Trp Val Ser Gln Leu Leu Gly Gly Met Leu
                155                 160                 165

Gly Ala Ala Leu Ala Lys Ala Val Ser Pro Glu Glu Arg Phe Trp
                170                 175                 180

Asn Ala Ser Gly Ala Ala Phe Val Thr Val Gln Glu Gln Gly Gln
                185                 190                 195
```

```
Val Ala Gly Ala Leu Val Ala Glu Ile Ile Leu Thr Thr Leu Leu
            200                 205                 210
Ala Leu Ala Val Cys Met Gly Ala Ile Asn Glu Lys Thr Lys Gly
            215                 220                 225
Pro Leu Ala Pro Phe Ser Ile Gly Phe Ala Val Thr Val Asp Ile
            230                 235                 240
Leu Ala Gly Gly Pro Val Ser Gly Gly Cys Met Asn Pro Ala Arg
            245                 250                 255
Ala Phe Gly Pro Ala Val Val Ala Asn His Trp Asn Phe His Trp
            260                 265                 270
Ile Tyr Trp Leu Gly Pro Leu Ala Gly Leu Leu Val Gly Leu
            275                 280                 285
Leu Ile Arg Cys Phe Ile Gly Asp Gly Lys Thr Arg Leu Ile Leu
            290                 295                 300
Lys Ala Arg Ser Arg Ala Arg Gly Ile Pro Ala Ala Pro Gly Val
            305                 310                 315
Leu Ser Ser Pro Val Pro Asp Gly Gln Gly Ser Ser Cys Ile Ser
            320                 325                 330
Cys Gln Gly Arg Gly Pro Glu Glu Arg Pro Pro Ala Ser Thr Ala
            335                 340                 345
Trp Ala Cys Phe Leu Arg Thr Asp Cys Gly Gly Ser Arg Phe Leu
            350                 355                 360
Glu Phe Leu Cys Ala His Gln Arg Pro Gln Pro Gly Glu His Ala
            365                 370                 375
Ala Arg Thr Ala Gln Arg Ala Val Gln Thr Pro Gln His Glu Arg
            380                 385                 390
Val Ser Glu Glu Cys Pro Arg Val Gly Gln Gly Cys Phe Cys
            395                 400                 405
Thr Ser Ala His Phe Pro His Pro Ile Ser Cys Leu Ile Ala Leu
            410                 415                 420
Leu Gly Ala Trp Pro Leu Pro Cys Phe Ser Ser Gln Phe Ser Leu
            425                 430                 435
Cys Asn Lys Ser Ser Val Ser Phe
            440

<210> SEQ ID NO 2
<211> LENGTH: 1354
<212> TYPE: DNA
<213> ORGANISM: Homo sapiens
<220> FEATURE:
<221> NAME/KEY: misc_feature
<223> OTHER INFORMATION: Incyte ID No: 2774542CB1
<300> PUBLICATION INFORMATION:

<400> SEQUENCE: 2
ggtgagccct ctgtcggcat cttcctctcc aggctggcag agcaagggggg gctgtgaatt     60 aattcaaggt tgggggtcgg ggccttctat atctggactt gcctcccacc cgtgtcctct    120
gtcccttttt ccctacggca gatagccatg tgtgagcctg aatttggcaa tgacaaggcc    180
agggagccga gcgtgggtgg caggtggcga gtgtcctggt acgaacggtt tgtgcagcca    240
tgtctggtcg aactgctggg ctctgctctc ttcatcttca tcgggtgcct gtcggtcatt    300
gagaatggga cggacactgg gctgctgcag ccggccctgg cccacgggct ggctttgggg    360
ctcgtgattg ccacgctggg gaatatcagt ggtggacact tcaaccctgc ggtgtccctg    420
gcagccatgc tgatcggagg cctcaacctg gtgatgctcc tcccgtactg ggtctcacag    480
```

```
ctgctcgggg ggatgctcgg ggctgccttg gccaaggcgg tgagtcctga ggagaggttc      540
tggaatgcat ctgggcggc ctttgtgaca gtccaggagc aggggcaggt ggcaggggcg       600
ttggtggcag agatcatcct gacgacgctg ctggccctgg ctgtatgcat gggtgccatc      660
aatgagaaga caaagggccc tctggccccg ttctccatcg gctttgccgt caccgtggat      720
atcctggctg ggggccctgt gtctggaggc tgcatgaatc ccgcccgtgc ttttggacct      780
gcggtggtgg ccaaccactg gaacttccac tggatctact ggctgggccc actcctggct      840
ggcctgcttg ttggactgct cattaggtgc ttcattggag atgggaagac ccgcctcatc      900
ctgaaggctc ggtgaagcag agctcgtggg attcctgctg ctccaggtgt cctcagctca      960
cctgtcccag actgaggaca ggggagttcc tgcatttcct gccagggcag aggcccagag     1020
gagcgacccc ctgcttccac tgcttgggcc tgctttctca gatagactga ctgctgagga     1080
ggctctaggt tcttggaatt cctttgtgct catcagagac cccagcctgg ggaacacgct     1140
gcccgcactg cccagagagc agtgcaaaca ccacaacacg agcgtgtttc ttgagaggaa     1200
tgtccccgag ttggacaagg aggctgtttc tgcacatcag ctcatttccc gcaccccatt     1260
tcttgcttga ttgctttgtt gggggcctgg ccacttcctt gcttctcaag ctgacaattc     1320
tcactttgca ataaatagtc cagtgtttcc ttcc                                 1354
```

<210> SEQ ID NO 3
<211> LENGTH: 233
<212> TYPE: DNA
<213> ORGANISM: Homo sapiens
<220> FEATURE:
<221> NAME/KEY: misc_feature
<223> OTHER INFORMATION: Incyte ID No: 2774542H1
<300> PUBLICATION INFORMATION:

<400> SEQUENCE: 3

```
ggtgagccct ctgtcggcat cttcctctcc aggctggcag agcaagggggg gctgtgaatt       60 aattcaaggt tgggggtcgg ggccttctat atctggactt gcctcccacc cgtgtcctct      120 gtccttttt cctacggca gatagccatg tgtgagcctg aatttggcaa tgacaaggcc        180
agggagccga gcgtgggtgg caggtggcga gtgtcctggt acgaacggtt tgt             233
```

<210> SEQ ID NO 4
<211> LENGTH: 274
<212> TYPE: DNA
<213> ORGANISM: Homo sapiens
<220> FEATURE:
<221> NAME/KEY: misc_feature
<223> OTHER INFORMATION: Incyte ID No: 3834902H1
<221> NAME/KEY: unsure
<222> LOCATION: 209
<223> OTHER INFORMATION: a, t, c, g, or other
<300> PUBLICATION INFORMATION:

<400> SEQUENCE: 4

```
cggcatcttc ctctccaggc tggcagagca aggggggctg tgaattaatt caaggttggg       60 gtcggggcc ttctatatct ggacttgcct cccaccgtg tcctctgtcc ttttttccct        120
acggcagata gccatgtgtg agcctgaatt tggcaatgac aaggccaggg agccgagcgt      180
gggtggcagg tggcgagtgt cctggtacna acgtttgtg cagccatgtc tggtcgaact      240 gctgggctc tgctctcttc atcttcatcg ggtg                                  274
```

<210> SEQ ID NO 5
<211> LENGTH: 1312
<212> TYPE: DNA

<213> ORGANISM: Homo sapiens
<220> FEATURE:
<221> NAME/KEY: misc_feature
<223> OTHER INFORMATION: Incyte ID No: 1804734CB1
<300> PUBLICATION INFORMATION:

<400> SEQUENCE: 5

| | | | | | |
|---|---|---|---|---|---|
| gtccctagga | gataagagta | tcttgcacag | caggtgcagg | tttcccagca | gctcaggcaa | 60 |
| gagtccgatg | tttgtgccat | ctgatcctga | tgtctggaga | gcagatagcc | atgtgtgagc | 120 |
| ctgaatttgg | caatgacaag | gccagggagc | cgagcgtggg | tggcaggtgg | cgagtgtcct | 180 |
| ggtacgaacg | gtttgtgcag | ccatgtctgg | tcgaactgct | gggctctgct | ctcttcatct | 240 |
| tcatcgggtg | cctgtcggtc | attgagaatg | gacggacac | tgggctgctg | cagccggccc | 300 |
| tggcccacgg | gctggctttg | gggctcgtga | ttgccacgct | ggggaatatc | agtggtggac | 360 |
| acttcaaccc | tgcggtgtcc | ctggcagcca | tgctgatcgg | aggcctcaac | ctggtgatgc | 420 |
| tcctcccgta | ctgggtctca | cagctgctcg | ggggatgct | cggggctgcc | ttggccaagg | 480 |
| cggtgagtcc | tgaggagagg | ttctggaatg | catctgggc | ggcctttgtg | acagtccagg | 540 |
| agcaggggca | ggtggcaggg | gcgttggtgg | cagagatcat | cctgacgacg | ctgctggccc | 600 |
| tggctgtatg | catgggtgcc | atcaatgaga | agacaaaggg | ccctctggcc | ccgttctcca | 660 |
| tcggctttgc | cgtcaccgtg | gatatcctgg | ctgggggccc | tgtgtctgga | ggctgcatga | 720 |
| atcccgcccg | tgcttttgga | cctgcggtgg | tggccaacca | ctggaacttc | cactggatct | 780 |
| actggctggg | cccactcctg | gctggcctgc | ttgttggact | gctcattagg | tgcttcattg | 840 |
| gagatgggaa | gacccgcctc | atcctgaagg | ctcggtgaag | cagagctcgt | gggattcctg | 900 |
| ctgctccagg | tgtcctcagc | tcacctgtcc | cagactgagg | acaggggagt | tcctgcattt | 960 |
| cctgccaggg | cagaggccca | gaggagcgac | cccctgcttc | cactgcttgg | gcctgctttc | 1020 |
| tcagatagac | tgactgctga | ggaggctcta | ggttcttgga | attcctttgt | gctcatcaga | 1080 |
| gaccccagcc | tggggaacac | gctgcccgca | ctgcccagag | agcagtgcaa | acaccacaac | 1140 |
| acgagcgtgt | tcttgagag | gaatgtcccc | gagttggaca | aggaggctgt | ttctgcacat | 1200 |
| cagctcattt | cccgcacccc | atttcttgct | tgattgcttt | gttggggggcc | tggccacttc | 1260 |
| cttgcttctc | aagctgacaa | ttctcacttt | gcaataaata | gtccagtgtt | tc | 1312 |

<210> SEQ ID NO 6
<211> LENGTH: 562
<212> TYPE: DNA
<213> ORGANISM: Homo sapiens
<220> FEATURE:
<221> NAME/KEY: misc_feature
<223> OTHER INFORMATION: Incyte ID No: 227165F1
<221> NAME/KEY: unsure
<222> LOCATION: 525, 550
<223> OTHER INFORMATION: a, t, c, g, or other
<300> PUBLICATION INFORMATION:

<400> SEQUENCE: 6

| | | | | | |
|---|---|---|---|---|---|
| ggaaggaaac | actggactat | ttattgcaaa | gtgagaattg | tcagcttgag | aagcaaggaa | 60 |
| gtggccaggc | cccaacaaa | gcaatcaaga | agaaatggg | gtgcgggaaa | tgagctgatg | 120 |
| tgcagaaaca | gcctccttgt | ccaactcggg | gacattcctc | tcaagaaaca | cgctcgtgtt | 180 |
| gtggtgtttg | cactgctctc | tggcagtgc | gggcagcgtg | ttccccaggc | tggggtctct | 240 |
| gatgagcaca | aaggaattcc | aagaacctag | agcctcctca | gcagtcagtc | tatctgagaa | 300 |
| agcaggccca | agcagtggaa | gcaggggtc | gctcctctgg | gcctctgccc | tggcaggaaa | 360 |

```
tgcaggaact cccctgtcct gagtctggga caggtgagct gaggacacct ggagcagcag      420
gaatcccacg agctctgttt caccgaggct tcaggatgag gcgggtcttt cccatcttcc      480
aatgaagcac ctaatgaggc agttccaaca aagcaggcca gccanggagt tgggcccagc      540
cagtaggatn ccagttggaa gt                                               562

<210> SEQ ID NO 7
<211> LENGTH: 620
<212> TYPE: DNA
<213> ORGANISM: Rattus norvegicus
<220> FEATURE:
<221> NAME/KEY: misc_feature
<223> OTHER INFORMATION: Incyte ID No: 701887401H1
<300> PUBLICATION INFORMATION:

<400> SEQUENCE: 7
ggacaggaca attccattat tttctgcagg acctgagctc agaggagcca ctctgacagc       60
agcaggtggc agaagccctg ggggtagaga tcgttatgac gatgctgttg gtattggctg      120
tatgtatggg tgccgtcaat gagaagacaa tgggtcccct agccccattc tccattggtt      180
tctctgtcat tgtggatatc ctggcaggtg gtgggatctc tggagcctgc atgaaccctg      240
ctcgtgcctt tggacctgct gtgatggctg gctactggga cttccattgg atctactggc      300
tgggcccact cctggctggc ctctttgtgg gactgctcat taggctcttc attggagatg      360
agaaaacccg cctgattcta aagtcgaggt gaagaactgc tggcagcatc cccactgcct      420
ggagtcctca gctgtttgtc ctgagttgag gacaggacaa ttccattatt ttctgcagga      480
cctggaactc ctttgtgccc atggactggg cttggggccc agcctaaaga caggtagaga      540
ccacatagaa aaggaggaca ggtctctgtt cttgagaaag ggcagggcat gggagagccg      600
agcaggtgga gcatgcagtt                                                  620

<210> SEQ ID NO 8
<211> LENGTH: 279
<212> TYPE: DNA
<213> ORGANISM: Rattus norvegicus
<220> FEATURE:
<221> NAME/KEY: misc_feature
<223> OTHER INFORMATION: Incyte ID No: 701624411H1
<300> PUBLICATION INFORMATION:

<400> SEQUENCE: 8
ttagaggaaa ggttctggaa tgcgtctggg gcagcctttg ccatagtcca ggagcaggag       60
caggtggcag aagccctggg ggtagagatc gttatgacga tgctgttggt attggctgtg      120
tgtatgggtg ccgtcaatga gaagaccatg gtcccctag ccccattctc cattggtttc      180
tctgtcattg tggatatcct ggcaagtggt gggatctctg agcctgcat gaaccctgct      240 cgtgcctttg gacctgctgt gatggctggc tactgggac                             279

<210> SEQ ID NO 9
<211> LENGTH: 159
<212> TYPE: DNA
<213> ORGANISM: Rattus norvegicus
<220> FEATURE:
<221> NAME/KEY: misc_feature
<223> OTHER INFORMATION: Incyte ID No: 701336587H1
<300> PUBLICATION INFORMATION:
```

-continued

```
<400> SEQUENCE: 9
gatcggagct gccctggcta aggtggtgag tccagaggaa aggttctgga atgcgtctgg    60
ggcagccttt gccatagtcc aggagcagga gcaggtggca gaagccctgg gggtagagat   120
cgttatgacg atgctgttgg tattggctgt atgtatggg                          159

<210> SEQ ID NO 10
<211> LENGTH: 325
<212> TYPE: DNA
<213> ORGANISM: Rattus norvegicus
<220> FEATURE:
<221> NAME/KEY: misc_feature
<223> OTHER INFORMATION: Incyte ID No: 701652485H1
<300> PUBLICATION INFORMATION:

<400> SEQUENCE: 10
ctccttcagc tggtgcagct cctggagctc tgactcccac cttccggtgc agatatgtct    60
ggggagacgc cgatgtgtag tatggaccta cgtgagatca aggggaagga gaccaacatg   120
gctgacagtt accatggcat gtcctggtat gagcagtaca taaccgtg tgtggtggaa    180 cttttgggct ccgctctctt catcttcatt gggtgtctat cggtcatcga aacagtcca    240 aatactgggc tcctgcagcc tgccctggct catgggctgg ccttggggct catcattgct   300
accttgggga acatcagcgg tggac                                         325

<210> SEQ ID NO 11
<211> LENGTH: 96
<212> TYPE: DNA
<213> ORGANISM: Rattus norvegicus
<220> FEATURE:
<221> NAME/KEY: misc_feature
<223> OTHER INFORMATION: Incyte ID No: 700938259H1
<300> PUBLICATION INFORMATION:

<400> SEQUENCE: 11
ttcggagctg ccctggctaa ggtggtgagt ccagaggaaa ggttctggaa tgcgtctggg    60
gcagcctttg ccatagtcca ggagcacgag caggtg                             96

<210> SEQ ID NO 12
<211> LENGTH: 263
<212> TYPE: PRT
<213> ORGANISM: Rattus norvegicus
<220> FEATURE:
<221> NAME/KEY: misc_feature
<223> OTHER INFORMATION: GenBank ID No.: g2346968
<300> PUBLICATION INFORMATION:

<400> SEQUENCE: 12

Met Ser Gly Glu Gln Thr Pro Met Cys Ser Met Asp Leu Arg Glu
  1               5                  10                  15

Ile Lys Gly Lys Glu Thr Asn Met Ala Asp Ser Tyr His Gly Met
                 20                  25                  30

Ser Trp Tyr Glu Gln Tyr Ile Gln Pro Cys Val Val Glu Leu Leu
                 35                  40                  45

Gly Ser Ala Leu Phe Ile Phe Ile Gly Cys Leu Ser Val Ile Glu
                 50                  55                  60

Asn Ser Pro Asn Thr Gly Leu Leu Gln Pro Ala Leu Ala His Gly
                 65                  70                  75

Leu Ala Leu Gly Leu Ile Ile Ala Thr Leu Gly Asn Ile Ser Gly
                 80                  85                  90
```

```
                                    -continued

Gly His Phe Asn Pro Ala Val Ser Leu Ala Val Thr Leu Val Gly
                 95              100              105

Gly Leu Lys Thr Met Leu Leu Ile Pro Tyr Trp Val Ser Gln Leu
                110              115              120

Phe Gly Gly Met Ile Gly Ala Ala Leu Ala Lys Val Val Ser Pro
                125              130              135

Glu Glu Arg Phe Trp Asn Ala Ser Gly Ala Ala Phe Ala Ile Val
                140              145              150

Gln Glu Gln Glu Gln Val Ala Glu Ala Leu Gly Val Glu Ile Val
                155              160              165

Met Thr Met Leu Leu Val Leu Ala Val Cys Met Gly Ala Val Asn
                170              175              180

Glu Lys Thr Met Gly Pro Leu Ala Pro Phe Ser Ile Gly Phe Ser
                185              190              195

Val Ile Val Asp Ile Leu Ala Gly Gly Gly Ile Ser Gly Ala Cys
                200              205              210

Met Asn Pro Ala Arg Ala Phe Gly Pro Ala Val Met Ala Gly Tyr
                215              220              225

Trp Asp Phe His Trp Ile Tyr Trp Leu Gly Pro Leu Leu Ala Gly
                230              235              240

Leu Phe Val Gly Leu Leu Ile Arg Leu Phe Ile Gly Asp Glu Lys
                245              250              255

Thr Arg Leu Ile Leu Lys Ser Arg
```

AQUAPORIN-8 VARIANT

AQUAPORIN-8 VARIANT

This application is a continuation-in-part of U.S. Ser. No. 09/226,994 filed Jan. 7, 1999 adadoned.

FIELD OF THE INVENTION

This invention relates to a mammalian cDNA which encodes a human aquaporin-8 variant and to the use of the cDNA and the encoded protein in the diagnosis and treatment of pancreatic disorders, particularly type I diabetes.

BACKGROUND OF THE INVENTION

Phylogenetic relationships among organisms have been demonstrated many times, and studies from a diversity of prokaryotic and eukaryotic organisms suggest a more or less gradual evolution of molecules, biochemical and physiological mechanisms, and metabolic pathways. Despite different evolutionary pressures, the proteins of nematode, fly, rat, and man have common chemical and structural features and generally perform the same cellular function. Comparisons of the nucleic acid and protein sequences from organisms where structure and/or function are known accelerate the investigation of human sequences and allow the development of model systems for testing diagnostic and therapeutic agents for human conditions, diseases, and disorders.

Aquaporins are ubiquitous water channel proteins belonging to the major intrinsic protein (MIP) superfamily of membrane proteins. Aquaporins contain sites which prevent ions from passing through the channel but allow water and certain other solutes such as urea and glycerol to pass through. Aquaporins are characterized by six membrane-spanning domains and five hydrophilic connecting loops containing two highly conserved asparagine-proline-alanine (NPA) amino acid motifs in the two halves of the protein. In mammals, aquaporins are found in exocrine glands such as the salivary glands and pancreas and in water-permeable epithelia of the lens, liver, testis, kidney, and colon. Aquaporin-8 (AQP8), discovered in rat pancreas and liver (Koyama et al. (1997) J Biol Chem 272:30329–30333), is highly homologous to plant γ- and α-tonoplast intrinsic proteins, also members of the MIP family. Similar to that of the plant aquaporin, γ-TIP, AQP8 has a longer N terminus and a shorter C terminus compared with those of other mammalian aquaporins (Koyama, supra). AQP8 does not allow transmembrane transport of urea or glycerol. AQP8 expression is strong in glandular lobes of the pancreas and parenchymal cells of the liver, testis and seminiferous tubules, and weak in acinal cells in the salivary gland and absorptive columnar epithelial cell layer of the colon.

The discovery of a mammalian, cDNA encoding aquaporin-8 variant satisfies a need in the art by providing compositions which are useful in the diagnosis and treatment of pancreatic disorders, particularly type I diabetes.

SUMMARY OF THE INVENTION

The invention is based on the discovery of a mammalian cDNA which encodes a mammalian aquaporin-8 variant (AQP8V) which is useful in the diagnosis and treatment of pancreatic disorders, particularly type I diabetes.

The invention provides an isolated mammalian cDNA or a fragment thereof encoding a mammalian protein or a portion thereof selected from the group consisting of an amino acid sequence of SEQ ID NO:1, a variant having 75% identity to the amino acid sequence of SEQ ID NO:1, an antigenic epitope of SEQ ID NO:1, an oligopeptide of SEQ ID NO:1, and a biologically active portion of SEQ ID NO:1. The invention also provides an isolated mammalian cDNA or the complement thereof selected from the group consisting of a nucleic acid sequence of SEQ ID NO:2, a variant having at least 81% identity to the nucleic acid sequence of SEQ ID NO:2, a fragment of SEQ ID NOs:3–11, an oligonucleotide of SEQ ID NOs:2–11. The invention additionally provides a composition, a substrate, and a probe comprising the cDNA ,or the complement of the cDNA, encoding AQP8V. The invention further provides a vector containing the cDNA, a host cell containing the vector and a method for using the cDNA to make AQP8V. The invention still further provides a transgenic cell line or organism comprising the vector containing the cDNA encoding AQP8V. The invention additionally provides a mammalian fragment or the complement thereof selected from the group consisting of SEQ ID NOs:3–11. In one aspect, the invention provides a substrate containing at least one of these fragments. In a second aspect, the invention provides a probe comprising the fragment which can be used in methods of detection, screening, and purification. In a further aspect, the probe is a single stranded complementary RNA or DNA molecule.

The invention provides a method for using a cDNA to detect the differential expression of a nucleic acid in a sample comprising hybridizing a probe to the nucleic acids, thereby forming hybridization complexes and comparing hybridization complex formation with a standard, wherein the comparison indicates the differential expression of the cDNA in the sample. In one aspect, the method of detection further comprises amplifying the nucleic acids of the sample prior to hybridization. In another aspect, the method showing differential expression of the cDNA is used to diagnose type I diabetes. In another aspect, the cDNA or a fragment or a complement thereof may comprise an element on an array.

The invention additionally provides a method for using a cDNA or a fragment or a complement thereof to screen a library or plurality of molecules or compounds to identify at least one ligand which specifically binds the cDNA, the method comprising combining the cDNA with the molecules or compounds under conditions allowing specific binding, and detecting specific binding to the cDNA, thereby identifying a ligand which specifically binds the cDNA. In one aspect, the molecules or compounds are selected from aptamers, DNA molecules, RNA molecules, peptide nucleic acids, artificial chromosome constructions, peptides, transcription factors, enhancers, repressors, and regulatory molecules.

The invention provides a purified mammalian protein or a portion thereof selected from the group consisting of an amino acid sequence of SEQ ID NO:1, an oligopeptide of SEQ ID NO:1, and a biologically active portion of SEQ ID NO:1. The invention also provides a composition comprising the purified protein or a portion thereof in conjunction with a pharmaceutical carrier. The invention further provides a method of using the AQP8V to treat a subject with type I diabetes comprising administering to a patient in need of such treatment the composition containing the purified protein. The invention still further provides a method for using a protein to screen a library or a plurality of molecules or compounds to identify at least one ligand the method comprising combining the protein with the molecules or compounds under conditions to allow specific binding and detecting specific binding, thereby identifying a ligand which specifically binds the protein. In one aspect, the molecules or compounds are selected from DNA molecules, RNA molecules, peptide nucleic acids, peptides, proteins, mimetics, agonists, antagonists, antibodies, immunoglobulins, inhibitors, and drugs. In another aspect, the ligand is used to treat a subject with type I diabetes.

The invention provides a method of using a mammalian protein to screen a subject sample for antibodies which specifically bind the protein comprising isolating antibodies from the subject sample, contacting the isolated antibodies with the protein under conditions that allow specific binding, dissociating the antibody from the bound-protein, and comparing the quantity of antibody with known standards, wherein the presence or quantity of antibody is diagnostic of type I diabetes.

The invention also provides a method of using a mammalian protein to prepare and purify antibodies comprising immunizing a animal with the protein under conditions to elicit an antibody response, isolating animal antibodies, attaching the protein to a substrate, contacting the substrate with isolated antibodies under conditions to allow specific binding to the protein, dissociating the antibodies from the protein, thereby obtaining purified antibodies.

The invention provides a purified antibody which binds specifically to AQP8V. The invention also provides a method of using an antibody to diagnose type I diabetes comprising combining the antibody comparing the quantity of bound antibody to known standards, thereby establishing the presence of type I diabetes. The invention further provides a method of using an antibody to treat type I diabetes comprising administering to a patient in need of such treatment a pharmaceutical composition comprising the purified antibody.

The invention provides a method for inserting a marker gene into the genomic DNA of a mammal to disrupt the expression of the endogenous polynucleotide. The invention also provides a method for using a cDNA to produce a mammalian model system, the method comprising constructing a vector containing the cDNA selected from SEQ ID NOs:2–11, transforming the vector into an embryonic stem cell, selecting a transformed embryonic stem, microinjecting the transformed embryonic stem cell into a mammalian blastocyst, thereby forming a chimeric blastocyst, transferring the chimeric blastocyst into a pseudopregnant dam, wherein the dam gives birth to a chimeric offspring containing the cDNA in its germ line, and breeding the chimeric mammal to produce a homozygous, mammalian model system.

BRIEF DESCRIPTION OF THE FIGURES AND TABLE

FIGS. 1A, 1B, 1C, and 1D show the mammalian AQP8V (SEQ ID NO:1) encoded by the cDNA (SEQ ID NO:2). The alignment was produced using MACDNASIS PRO software (Hitachi Software Engineering, South San Francisco Calif.).

FIG. 2 demonstrates the conserved chemical and structural similarities among the transmembrane domains of AQP8V (2774542CD1; SEQ ID NO:1 ) and Rattus norvegicus aquaporin-8 (g2346968), SEQ ID NO:12. The alignment was produced using the MEGALIGN program of LASERGENE software (DNASTAR, Madison Wis.).

FIG. 3 show the highly specific differential expression of AQP8V in pancreas and particularly in tissues with type I diabetes. The northern analysis was produced using the LIFESEQ Gold database (Incyte Genomics, Palo Alto Calif.).

FIG. 4 shows the hydrophilicity plots and antigenic indices for AQP8V (2774542CD1; SEQ ID NO:1) and rat AQP8 (g2346968).

DESCRIPTION OF THE INVENTION

It is understood that this invention is not limited to the particular machines, materials and methods described. It is also to be understood that the terminology used herein is for the purpose of describing particular embodiments and is not intended to limit the scope of the present invention which will be limited only by the appended claims. As used herein, the singular forms "a", "an", and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"AQP8V" refers to a substantially purified protein obtained from any mammalian species, including bovine, canine, murine, ovine, porcine, rodent, simian, and preferably the human species, and from any source, whether natural, synthetic, semi-synthetic, or recombinant.

"Array" refers to an ordered arrangement of at least two cDNAs on a substrate. At least one of the cDNAs represents a control or standard sequence, and the other, a cDNA of diagnostic interest. The arrangement of from about two to about 40,000 cDNAs on the substrate assures that the size and signal intensity of each labeled hybridization complex formed between a cDNA and a sample nucleic acid is individually distinguishable.

The "complement" of a cDNA of the Sequence Listing refers to a nucleic acid molecule which is completely complementary over its full length and which will hybridize to the cDNA or an mRNA under conditions of high stringency.

"cDNA" refers to an isolated polynucleotide, nucleic acid molecule, or any fragment or complement thereof. It may have originated recombinantly or synthetically, be double-stranded or single-stranded, represent coding and/or non-coding sequence, an exon with or without an intron from a genomic DNA molecule.

The phrase "cDNA encoding a protein" refers to a nucleic acid sequence that closely aligns with sequences which encode conserved regions, motifs or domains that were identified by employing analyses well known in the art. These analyses include BLAST (Basic Local Alignment Search Tool; Altschul (1993) J Mol Evol 36: 290–300; Altschul et al. (1990) J Mol Biol 215:403–410) which provides identity within the conserved region.

"Derivative" refers to a cDNA or a protein that has been subjected to a chemical modification. Derivatization of a cDNA can involve substitution of a nontraditional base such as queosine or of an analog such as hypoxanthine. These substitutions are well known in the art. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity. "Differential expression" refers to an increased, upregulated or present, or decreased, downregulated or absent, gene expression as detected by the absence, presence, or at least two-fold changes in the amount of transcribed messenger RNA or translated protein in a sample.

"Disorder" refers to conditions, diseases or syndromes of the pancreas or co-regulated within it in which the cDNAs and AQP8V are differentially expressed, including specifically type I diabetes.

"Fragment" refers to a chain of consecutive nucleotides from about 200 to about 700 base pairs in length. Fragments may be used in PCR or hybridization technologies to identify related nucleic acid molecules and in binding assays to screen for a ligand. Nucleic acids and their ligands identified in this manner are useful as therapeutics to regulate replication, transcription or translation.

"GBA" is the acronym for guilt-by-association, a method for identifying biomolecules that are co-expressed with known genes in a plurality of cDNA libraries and that are associated with a specific disease, regulatory pathway, subcellular compartment, cell type, tissue type, or species. In this case, the known genes were involved specifically with insulin-synthesis.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. The degree of complementarity and the use of nucleotide analogs affect the efficiency and stringency of hybridization reactions.

"Ligand" refers to any agent, molecule, or compound which will bind specifically to a complementary site on a cDNA molecule or polynucleotide, or to an epitope or a protein. Such ligands stabilize or modulate the activity of polynucleotides or proteins and may be composed of inorganic or organic substances including nucleic acids, proteins, carbohydrates, fats, and lipids.

"Oligonucleotide" refers a single stranded molecule from about 18 to about 60 nucleotides in length which may be used in hybridization or amplification technologies or in regulation of replication, transcription or translation. Substantially equivalent terms are amplimer, primer, and oligomer.

"Portion" refers to any part of a protein used for any purpose; but especially, to an epitope for the screening of ligands or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA that hybridizes to at least one nucleic acid in a sample. Where targets are single stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein refers to that length of amino acid sequence which would retain at least one biological activity, a domain identified by PFAM or PRINTS analysis or an antigenic epitope of the protein identified using Kyte-Doolittle algorithms of the PROTEAN program (DNASTAR, Madison Wis.). An "oligopeptide" is an amino acid sequence from about five residues to about 15 residues that is used as part of a fusion protein to produce an antibody.

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint, buccal cells, skin, or hair; and the like.

"Specific binding" refers to a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

"Similarity" as applied to sequences, refers to the quantification (usually percentage) of nucleotide or residue matches between at least two sequences aligned using a standardized algorithm such as Smith-Waterman alignment (Smith and Waterman (1981) J Mol Biol 147:195–197) or BLAST2 (Altschul et al. (1997) Nucleic Acids Res 25:3389–3402). BLAST2 may be used in a standardized and reproducible way to insert gaps in one of the sequences in order to optimize alignment and to achieve a more meaningful comparison between them.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to molecules that are recognized variations of a cDNA or a protein encoded by the cDNA. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid

THE INVENTION

The invention is based on the discovery of a cDNA which encodes AQP8V and on the use of the cDNA, or fragments thereof, and protein, or portions thereof, directly or as compositions in the characterization, diagnosis, and treatment of type I diabetes.

The cDNA encoding AQP8V of the present invention was first identified as an aquaporin-8 through GBA analysis of sequences co-regulated in insulin synthesis pathways. Nine known insulin-synthesis genes were selected to identify novel genes that are closely associated with insulin-synthesis. These known genes were insulin, glucagon, regenerating genes, lipase, colipase, and human islet amyloid polypeptide. The degree of association was measured by probability values and had a cutoff p value of less than 0.00001. This was followed by annotation and literature searches to insure that the genes that passed the probability test had strong associations with known insulin-synthesis genes. Thirteen novel genes showed strong association with known insulin-synthesis genes from a total of 41,419 assembled gene sequences.

The full length cDNA, SEQ ID NO:2, as shown in FIG. 1, was assembled and sequenced from the LIFESEQ databases (Incyte Genomics) and Incyte Clones (library), 2774542H1 (PANCNOT15), 3834902H1 (PANCNOT17), 1804734CB1 (SINTNOT13), and 277165F1 (PANCNOT01), which are SEQ ID NOs:3–6, respectively. Aquaporin 8 variant cDNA is 1354 nucleic acids in length. The BLAST2 homology between Incyte Clone 2774542CB1 and the rat MRNA (g2346967) that codes for AQP8V (g2346968), a member of water channel proteins identified from rat testis that contains the conserved transmembrane domains of the major intrinsic protein (MIP) family, is 81%.

FIG. 3 shows highly differential expression of the cDNA in pancreas from subjects with type I diabetes; therefore, the cDNA encoding AQP8V is useful as a diagnostic for type I diabetes. All of these libraries were from pancreas; two were associated with type I diabetes; two with islet cells. FIG. 3 shows the highly differential expression of AQP8V in pancreas from subjects with type I diabetes and the low levels of AQP8V expression in pancreas from subjects with other diseases or disorders. A fragment of SEQ ID NO:2 from nucleotide 1 to nucleotide 200 is useful as a hybridization probe. An oligonucleotide from 90 to 105 or 185 to 200 is useful as a diagnostic to distinguishing AQP8V from other aquaporins.

In one embodiment, the invention encompasses a polypeptide comprising the amino acid sequence of SEQ ID NO:1. BLIMPS analysis shows that SEQ ID NO:1 has six conserved amino acid segments that match the conserved transmembrane domains of the MIP family proteins. These segments encompass amino acid residues 30 to 49, 66 to 90, 103 to 122, 154 to 172, 185 to 207, and 222 to 242. Both HMM transmembrane and LASERGENE software (DNASTAR) analyses confirm these domains.

Figure 2:
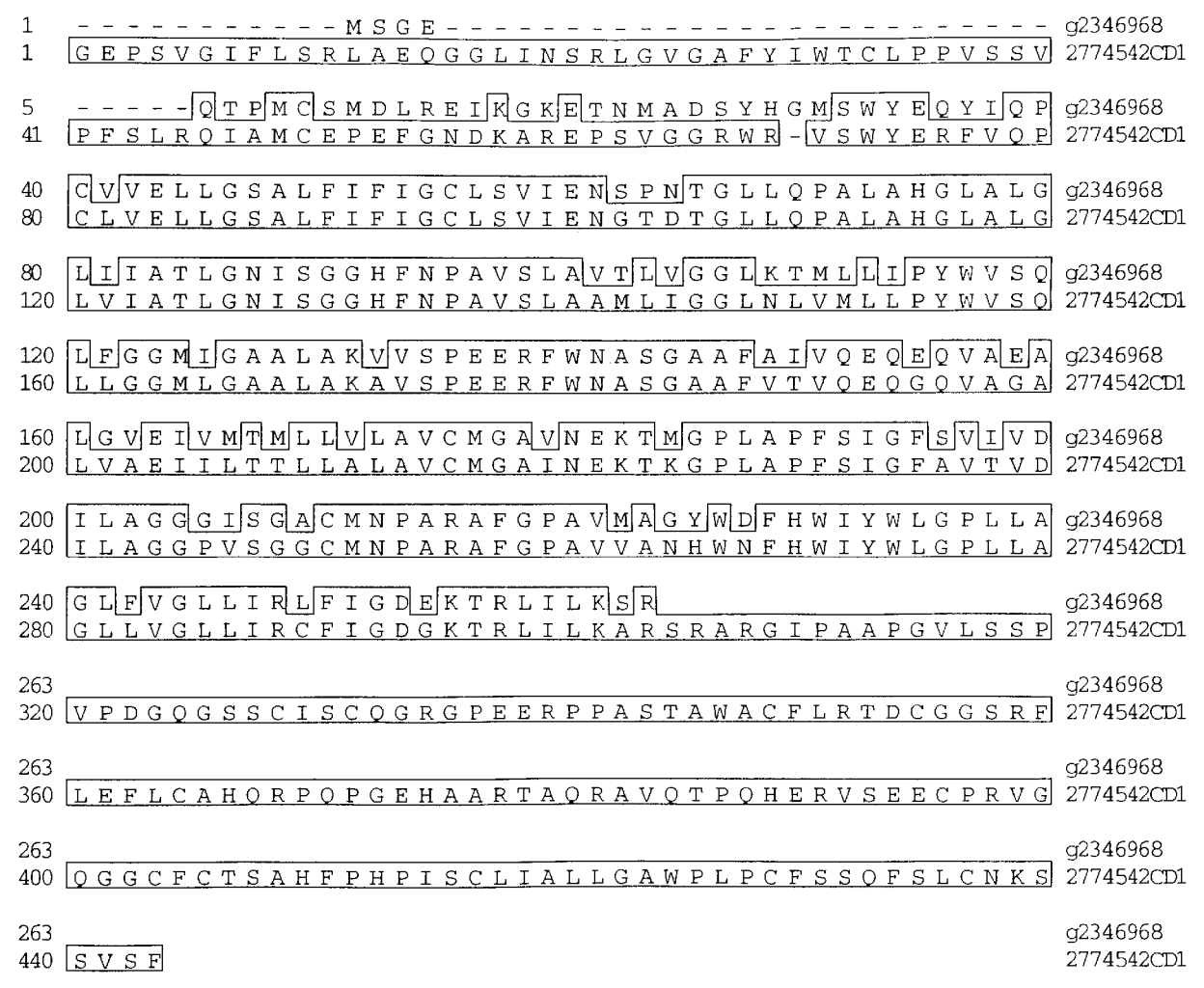

SEQ ID NO:1 is used as the reference for numbering the conserved residues, and MIP motifs, of the proteins (SEQ ID NOs:1 and 12) in the alignment, shown in FIG. 2. The residues, motifs and subdomains are: subdomain 1 extending from F28 to I239; and two invariant MIP family NPA motifs, one from residue 86 to residue 88 and the other from residue 104 to residue 106. Exemplary portions of SEQ ID NO:1 are antigenic epitopes, residue 51 to residue 59, residue 125 to residue 132, residue 171 to residue 179, and residue 243 to residue 250 of SEQ ID NO:1 (LASERGENE software; DNASTAR), as shown in FIG. 4A.

Mammalian variants of the cDNA encoding AQP8V were identified using BLAST or BLAST2, with default parameters and the LIFESEQ or ZOOSEQ databases (Incyte Genomics). Mammalian variants of the human nucleic acid sequence are Incyte clones (and their libraries) and include 701887401 (RALITXS02), 701624411 (RALITXT83), 701336587H1 (RALINON08), 701652485 (RALITXT10), and 700938259 (RALINON03); SEQ ID NOs:7–11, respectively, of the Sequence Listing. These cDNAs are particularly useful for producing transgenic cell lines or organisms which model human disorders and upon which potential therapeutic treatments for such disorders may be tested Table 1 below shows the percent identity between the cDNA encoding AQP8V and its mammalian variants, SEQ ID NOs:7–11. The first column shows the SEQ ID for the human cDNA; the second column, the SEQ IDvar for variant cDNAs; the third column, the clone number for the variant cDNAs; the fourth column, the percent identity to the human cDNA; and the fifth column, the alignment of the variant cDNA to the human cDNA.

| SEQ ID$_H$ | SEQ ID$_{var}$ | Clone$_{var}$ | Identity | Nt$_H$ Alignment |
| --- | --- | --- | --- | --- |
| 2 | 7 | 701887401 | 83% | 638–896 |
| 2 | 8 | 701624411 | 81% | 529–728 |
| 2 | 9 | 701336587 | 87% | 497–595 |
| 2 | 10 | 701652485 | 82% | 257–397 |
| 2 | 11 | 700938259 | 86% | 497–591 |

It will be appreciated by those skilled in the art that as a result of the degeneracy of the genetic code, a multitude of cDNA encoding AQP8V, some bearing minimal similarity to the cDNAs of any known and naturally occurring gene, may be produced. Thus, the invention contemplates each and every possible variation of cDNA that could be made by selecting combinations based on possible codon choices. These combinations are made in accordance with the standard triplet genetic code as applied to the polynucleotide encoding naturally occurring AQP8V, and all such variations are to be considered as being specifically disclosed.

The cDNA and fragments thereof (SEQ ID NOs:2–11) may be used in hybridization, amplification, and screening technologies to identify and distinguish among SEQ ID NO:2 and related molecules in a sample. The mammalian cDNAs may be used to produce transgenic cell lines or organisms which are model systems for human type I diabetes and upon which the toxicity and efficacy of potential therapeutic treatments may be tested. Toxicology studies, clinical trials, and subject/patient treatment profiles may be performed and monitored using the cDNAs, proteins, antibodies and molecules and compounds identified using the cDNAs and proteins of the present invention.

Characterization and Use of the Invention
cDNA libraries

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. Three library preparations representative of the invention are described in the EXAMPLES below. The consensus sequences were chemically and/or electronically assembled from fragments including Incyte clones and extension and/or shotgun sequences using computer programs such as PHRAP (Phil Green, University of Washington, Seattle Wash.), and AUTOASSEMBLER application (PE Biosystems, Foster City Calif.). Clones, extension and/or shotgun sequences are electronically assembled into clusters and/or master clusters.

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech (APB), Piscataway N.J.), or combinations of polymerases and proofreading exonucleases such as those found in the ELONGASE amplification system (Life Technologies, Gaithersburg Md.).

Preferably, sequence preparation is automated with machines such MICROLAB 2200 system (Hamilton, Reno Nev.) and the DNA ENGINE thermal cycler (MJ Research, Watertown Mass.). Machines commonly used for sequencing include the ABI PRISM 3700, 377 or 373 DNA sequencing systems (PE Biosystems), the MEGABACE 1000 DNA sequencing system (APB), and the like. The sequences may be analyzed using a variety of algorithms well known in the art and described in Ausubel et al. (1997; *Short Protocols in Molecular Biology*, John Wiley & Sons, New York N.Y., unit 7.7) and in Meyers (1995; *Molecular Biology and Biotechnology*, Wiley VCH, New York N.Y., pp. 856–853).

Shotgun sequencing may also be used to complete the sequence of a particular cloned insert of interest. Shotgun strategy involves randomly breaking the original insert into segments of various sizes and cloning these fragments into vectors. The fragments are sequenced and reassembled using overlapping ends until the entire sequence of the original insert is known. Shotgun sequencing methods are well known in the art and use thermostable DNA polymerases, heat-labile DNA polymerases, and primers chosen from representative regions flanking the cDNAs of interest. Incomplete assembled sequences are inspected for identity using various algorithms or programs such as CONSED (Gordon (1998) Genome Res 8:195–202) which are well known in the art. Contaminating sequences including vector or chimeric sequences or deleted sequences can be removed or restored, respectively, organizing the incomplete assembled sequences into finished sequences.

Extension of a Nucleic Acid Sequence

The sequences of the invention may be extended using various PCR-based methods known in the art. For example, the XL-PCR kit (PE Biosystems), nested primers, and commercially available cDNA or genomic DNA libraries may be used to extend the nucleic acid sequence. For all PCR-based methods, primers may be designed using commercially available software, such as OLIGO 4.06 primer analysis software (National Biosciences, Plymouth Minn.) to be about 22 to 30 nucleotides in length, to have a GC content of about 50% or more, and to anneal to a target molecule at temperatures from about 55C to about 68C. When extending a sequence to recover regulatory elements, it is preferable to use genonic, rather than cDNA libraries.

Hybridization

The cDNA and fragments thereof can be used in hybridization technologies for various purposes. A probe may be designed or derived from unique regions such as the 5' regulatory region or from a nonconserved region (i.e., 5' or 3' of the nucleotides encoding the conserved catalytic domain of the protein) and used in protocols to identify naturally occurring molecules encoding the AQP8V, alletic variants, or related molecules. The probe may be DNA or RNA, may be single stranded and should have at least 50% sequence identity to any of the nucleic acid sequences, SEQ ID NOs:2–11. Hybridization probes may be produced using oligolabeling, nick translation, end-labeling, or PCR amplification in the presence of a reporter molecule. A vector containing the cDNA or a fragment thereof may be used to produce an MnRNA probe in vitro by addition of an RNA polymerase and labeled nucleotides. These procedures may be conducted using commercially available kits such as those provided by APB.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60C, which permits the formation of a hybridization complex between nucleic acid sequences that contain some mismatches. Subsequent washes are performed at higher stringency with buffers such as 0.2×SSC with 0.1% SDS at either 45C (medium stringency) or 68C (high stringency). At high stringency, hybridization complexes will remain stable only where the nucleic acids are completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or TRITON X-100 (Sigma-Aldrich, St. Louis Mo.) and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Arrays may be prepared and analyzed using methods known in the art. Oligonucleotides may be used as either probes or targets in an array. The array can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc Natl Acad Sci 93:10614–10619; Baldeschweiler et al. (1995) PCT application WO95/251116; Shalon et al. (1995) PCT application WO95/35505; Heller et al. (1997) Proc Natl Acad Sci 94:2150–2155; and Heller et al. (1997) U.S. Pat. No. 5,605,662.).

Hybridization probes are also useful in mapping the naturally occurring genomic sequence. The probes may be hybridized to: 1) a particular chromosome, 2) a specific region of a chromosome, or 3) an artificial chromosome construction such as human artificial chromosome (HAC), yeast artificial chromosome (YAC), bacterial artificial chromosome (BAC), bacterial P1 construction, or single chromosome cDNA libraries.

Expression

Any one of a multitude of cDNAs encoding AQP8V may be cloned into a vector and used to express the protein, or portions thereof, in host cells. The nucleic acid sequence can be engineered by such methods as DNA shuffling (U.S. Pat. No. 5,830,721) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, cDNA, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β glucuronidase, luciferase and the like, may be propagated using culture techniques. Visible markers are also used to quantify the amount of protein expressed by the introduced genes. Verification that the host cell contains the desired mammalian cDNA is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), 6×His, FLAG, MYC, and the like. GST and 6-His are purified using commercially available affinity matrices such as immobilized glutathione and metal-chelate resins, respectively. FLAG and MYC are purified using commercially available monoclonal and polyclonal antibodies. For ease of separation following purification, a sequence encoding a proteolytic cleavage site may be part of the vector located between the protein and the heterologous moiety. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N, N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1-S20). Automated synthesis may also be carried out on machines such as the ABI431A peptide synthesizer (PE Biosystems). A protein or portion thereof may be substantially purified by preparative high performance liquid chromatography and its composition confirmed by amino acid analysis or by sequencing (Creighton (1984) *Proteins, Structures and Molecular Properties*, WH Freeman, New York N.Y.).

Preparation and Screening of Antibodies

Various hosts including goats, rabbits, rats, mice, humans, and others may be immunized by injection with AQP8V or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol Methods 81:3142; Cote et al. (1983) Proc Natl Acad Sci 80:2026–2030; and Cole et al. (1984) Mol Cell Biol 62:109–120.)

Alternatively, techniques described for the production of single chain antibodies may be adapted, using methods known in the art, to produce epitope specific single chain antibodies. Antibody fragments which contain specific binding sites for epitopes of the protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) *Science* 246:1275–1281.).

The AQP8V or a portion thereof may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of reporter molecules and conjugation techniques are known by those skilled in the art and may be used in various nucleic acid, amino acid, and antibody assays. Synthesis of labeled molecules may be achieved using commercially available kits (Promega, Madison Wis.) for incorporation of a labeled nucleotide such as $^{32}$P-dCTP (APB), Cy3-dCTP or Cy5-dCTP (Operon Technologies, Alameda Calif.), or amino acid such as $^{35}$S-methionine (APB). Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

DIAGNOSTICS

The cDNAs, fragments, oligonucleotides, complementary RNA and DNA molecules, and PNAs and may be used to detect and quantify differential gene expression, absence/ presence vs. excess, expression of mRNAs or to monitor mRNA levels during therapeutic intervention. Similarly antibodies which specifically bind AQP8V may be used to quantitate the protein. Pancreatic disorders associated with differential expression include specifically type I diabetes. The diagnostic assay may use hybridization or amplification technology to compare gene expression in a biological sample from a patient to standard samples in order to detect differential gene expression. Qualitative or quantitative methods for this comparison are well known in the art.

For example, the cDNA or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human, with a cDNA under conditions for hybridization to occur. Standard hybridization complexes may be quantified by comparing the values obtained using normal subjects with values from an experiment in which a known amount of a substantially purified sequence is used. Standard values obtained in this manner may be compared with values obtained from samples from patients who were diagnosed with a particular condition, disease, or disorder. Deviation from standard values toward those associated with a particular disorder is used to diagnose that disorder.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed. (See, e.g., Coligan et al. (1997) *Current Protocols in Immunology*, Wiley-Interscience, New York N.Y.; and Pound, supra.).

THERAPEUTICS

Chemical and structural similarities, in the context of the two invariant MIP family NPA motifs, exist between regions of AQP8V (SEQ ID NO:1) and the GenBank homolog shown in FIG. 2 for SEQ ID NO:12. In addition, differential expression is highly associated with tissues and with type I diabetes as shown in FIG. 3 and hydrophilicity data as shown in FIG. 4A. AQP8V clearly plays a role in type I diabetes.

In the treatment of conditions associated with increased expression of the protein such as type I diabetes, it is desirable to decrease expression or protein activity. In one embodiment, an inhibitor, antagonist or antibody of the protein may be administered to a subject to treat a condition associated with increased expression or activity. In another embodiment, a pharmaceutical composition comprising an inhibitor, antagonist or antibody in conjunction with a pharmaceutical carrier may be administered to a subject to treat a condition associated with the increased expression or activity of the endogenous protein. In an additional embodiment, a vector expressing the complement of the cDNA or fragments thereof may be administered to a subject to treat the disorder.

Any of the cDNAs, complementary molecules, or fragments thereof, proteins or portions thereof, vectors delivering these nucleic acid molecules or expressing the proteins, and their ligands may be administered in combination with other therapeutic agents. Selection of the agents for use in combination therapy may be made by one of ordinary skill in the art according to conventional pharmaceutical principles. A combination of therapeutic agents may act synergistically to affect treatment of a particular disorder at a lower dosage of each agent.

Modification of Gene Expression Using Nucleic Acids

Gene expression may be modified by designing complementary or antisense molecules (DNA, RNA, or PNA) to the control, 5', 3', or other regulatory regions of the gene encoding AQP8V. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immnunologic Approaches*, Futura Publishing, Mt. Kisco N.Y., pp. 163–177). A complementary molecule may also be designed to block translation by preventing binding between ribosomes and mRNA. In one alternative, a library or plurality of cDNAs or fragments thereof may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2'O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

Screening and Purification Assays

The cDNA encoding AQP8V may be used to screen a library of molecules or compounds for specific binding affinity. The libraries may be aptamers, DNA molecules, RNA molecules, PNAs, artificial chromosome constructions, peptides, proteins such as transcription factors, enhancers, repressors, and other ligands which regulate the activity, replication, transcription, or translation of the cDNA in the biological system. The assay involves combining the cDNA or a fragment thereof with the library of molecules under conditions allowing specific binding, and detecting specific binding to identify at least one molecule which specifically binds the single stranded or, if appropriate, double stranded molecule.

In one embodiment, the cDNA of the invention may be incubated with a library of isolated and purified molecules or compounds and binding activity determined by methods well known in the art, e.g., a gel-retardation assay (U.S. Pat. No. 6,010,849) or a reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay and may be later confirmed by raising antibodies against that molecule or compound. When these antibodies are added into the assay, they cause a supershift in the gel-retardation assay.

In another embodiment, the cDNA may be used to purify a molecule or compound using affinity chromatography methods well known in the art. In one embodiment, the cDNA is chemically reacted with cyanogen bromide groups on a polymeric resin or gel. Then a sample is passed over and reacts with or binds to the cDNA. The molecule or compound which is bound to the cDNA may be released from the cDNA by increasing the salt concentration of the flow-through medium and collected.

In a further embodiment, the protein or a portion thereof may be used to purify a ligand from a sample. A method for using a mammalian protein or a portion thereof to purify a ligand would involve combining the protein or a portion thereof with a sample under conditions to allow specific binding, detecting specific binding between the protein and ligand, recovering the bound protein, and using an appropriate chaotropic agent to separate the protein from the purified ligand.

In a preferred embodiment, AQP8V or a portion thereof may be used to screen a plurality of molecules or compounds in any of a variety of screening assays. The portion of the protein employed in such screening may be free in solution, affixed to an abiotic or-biotic substrate (e.g. borne on a cell surface), or located intracellularly. For example, in one method, viable or fixed prokaryotic host cells that are stably transformed with recombinant nucleic acids that have expressed and positioned a peptide on their cell surface can be used in screening assays. The cells are screened against a plurality or libraries of ligands and the specificity of binding or formation of complexes between the expressed protein and the ligand may be measured. Specific binding between the protein and molecule may be measured. Depending on the kind of library being screened, the assay may be used to identify DNA molecules, RNA molecules, peptide nucleic acids, peptides, proteins, mimetics, agonists, antagonists, antibodies, immunoglobulins, inhibitors, and drugs or any other ligand, which specifically binds the protein.

In one aspect, this invention comtemplates a method for high throughput screening using very small assay volumes and very small amounts of test compound as described in U.S. Pat. No. 5,876,946, incorporated herein by reference. This method is used to screen large numbers of molecules and compounds via specific binding. In another aspect, this invention also contemplates the use of to competitive drug screening assays in which neutralizing antibodies capable of binding the protein specifically compete with a test compound capable of binding to the protein or oligopeptide or portion thereof. Molecules or compounds identified by screening may be used in a mammalian model system to evaluate their toxicity, diagnostic, or therapeutic potential.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$.

Pharmaceutical compositions which exhibit large therapeutic indexes are preferred. The data obtained from cell culture assays and animal studies are used in formulating a range of dosage for human use.

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice. Observation of qualitative and quantitative changes in physiology, behavior, homeostatic processes, and lethality in the rats or mice are used to generate a toxicity profile and to assess potential consequences on human health following exposure to the agent.

Genetic toxicology identifies and analyzes the effect of an agent on the rate of endogenous, spontaneous, and induced genetic mutations. Genotoxic agents usually have common chemical or physical properties that facilitate interaction with nucleic acids and are most harmful when chromosomal aberrations are transmitted to progeny. Toxicological studies may identify agents that increase the frequency of structural or functional abnormalities in the tissues of the progeny if administered to either parent before conception, to the mother during pregnancy, or to the developing organism. Mice and rats are most frequently used in these tests because their short reproductive cycle allows the production of the numbers of organisms needed to satisfy statistical requirements.

Acute toxicity tests are based on a single administration of an agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Subchronic toxicity tests are based on the repeated administration of an agent. Rat and dog are commonly used in these studies to provide data from species in different families. With the exception of carcinogenesis, there is considerable evidence that daily administration of an agent at highdose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents that over-express or under-express a gene of interest may be inbred and used to model human diseases or to test therapeutic or toxic agents. (See, e.g., U.S. Pat. No. 5,175,383 and U.S. Pat. No. 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells are placed inside a carrier embryo, they resume normal development and contribute to tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors used to produce a transgenic strain contain a disease gene candidate and a marker gen, the latter serves to identify the presence of the introduced disease gene. The vector is transformed into ES cells by methods well known in the art, and transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains.

ES cells derived from human blastocysts may be manipulated in vitro to differentiate into at least eight separate cell lineages. These lineages are used to study the differentiation of various cell types and tissues in vitro, and they include endoderm, mesoderm, and ectodermal cell types which differentiate into, for example, neural cells, hematopoietic lineages, and cardiomyocytes.

Knockout Analysis

In gene knockout analysis, a region of a mammalian gene is enzymatically modified to include a non-mammalian gene such as the neomycin phosphotransferase. gene (neo; Capecchi (1989) Science 244:1288–1292). The modified gene is transformed into cultured ES cells and integrates into the endogenous genome by homologous recombination. The inserted sequence disrupts transcription and translation of the endogenous gene. Transformed cells are injected into rodent blastulae, and the blastulae are implanted into pseudopregnant dams. Transgenic progeny are crossbred to obtain homozygous inbred lines which lack a functional copy of the mammalian gene. In one example, the mammalian gene is a human gene.

Knockin Analysis

ES cells can be used to create knockin humanized animals (pigs) or transgenic animal models (mice or rats) of human diseases. With knockin technology, a region of a human gene is injected into animal ES cells, and the human sequence integrates into the animal cell genome. Transformed cells are injected into blastulae and the blastulae are implanted as described above. Transgenic progeny or inbred lines are studied and treated with potential pharmaceutical agents to obtain information on treatment of the analogous human condition. These methods have been used to model several human diseases.

In additional embodiments, the cDNAs which encode the mammalian protein may be used in any molecular biology techniques that have yet to be developed, provided the new techniques rely on properties of cDNAs that are currently known, including, but not limited to, such properties as the triplet genetic code and specific base pair interactions.

EXAMPLES

The examples below are provided to illustrate the subject invention and are not included for the purpose of limiting the invention. For purposes of example, preparation of the human pancreas (PANCNOT15) library will be described.

I cDNA Library Construction

The tissue used for pancreas library construction was obtained from a 15-year-old Caucasian male during a exploratory laparotomy with distal pancreatectomy and total splenectomy. The frozen tissue was homogenized and lysed in TRIZOL reagent (1 g tissue/10 ml TRIZOL; Life Technologies) using a Polytron homogenizer (Brinkmann Instruments, Westbury N.Y.). After brief incubation on ice, chloroform was added (1:5 v/v), and the mixture was centrifuged to separate the phases. The upper aqueous phase was removed to a fresh tube, and isopropanol was added to precipitate RNA. The RNA was resuspended in RNase-free water and treated with DNase. The RNA was re-extracted with acid phenol-chloroform and reprecipitated with sodium acetate and ethanol. Poly(A+) RNA was isolated using the OLIGOTEX mRNA purification kit (QIAGEN, Valencia Calif.).

II Construction of pINCY Plasmid

The plasmid was constructed by digesting the pSPORT1 plasmid (Life Technologies) with EcoRI restriction enzyme (New England Biolabs, Beverly Mass.) and filling the overhanging ends using Klenow enzyme (New England Biolabs) and 2'-deoxynucleotide 5'-triphosphates (dNTPs). The plasmid was self-ligated and transformed into the bacterial host, E. coli strain JM109.

An intermediate plasmid produced by the bacteria (pSPORT1-ΔRI) showed no digestion with EcoRI and was digested with Hind III (New England Biolabs) and the overhanging ends were again filled in with Klenow and dNTPs. A linker sequence was phosphorylated, ligated onto the 5' blunt end, digested with EcoRI, and self-ligated. Following transformation into JM109 host cells, plasmids were isolated and tested for preferential digestibility with EcoRI, but not with Hind III. A single colony that met this criteria was designated pINCY plasmid.

After testing the plasmid for its ability to incorporate cDNAs from a library prepared using NotI and EcoRI restriction enzymes, several clones were sequenced; and a single clone containing an insert of approximately 0.8 kb was selected from which to prepare a large quantity of the plasmid. After digestion with NotI and EcoRI, the plasmid was isolated on an agarose gel and purified using a QIAQUICK column (Qiagen) for use in library construction.

III Isolation and Sequencing of cDNA Clones

Plasmid DNA was released from the cells and purified using either the MINIPREP Kit (Edge Biosystems, Gaithersburg Md.) or the REAL PREP 96 plasmid kit (Qiagen). This kit consists of a 96-well block with reagents for 960 purifications. The recommended protocol was employed except for the following changes: 1) the bacteria were cultured in 1 ml of sterile TERRIFIC BROTH (BD Biosciences, Sparks Md.) with carbenicillin at 25 mg/l and glycerol at 0.4%; 2) after inoculation, the cells were its cultured for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4 C.

The cDNAs were prepared for sequencing using the MICROLAB 2200 system (Hamilton) in combination with the DNA ENGINE thermal cyclers (MJ Research). The cDNAs were sequenced by the method of Sanger and Coulson (1975; J Mol Biol 94:441–448) using an ABI PRISM 377 sequencing system (PE Biosystems) or the MEGABACE 1000 DNA sequencing system (APB). Most of the isolates were sequenced according to standard ABI protocols and kits (PE Biosystems) with solution volumes of 0.25×–1.0× concentrations. In the alternative, cDNAs were sequenced using solutions and dyes from APB.

IV Co-expression Analyses of Insulin-synthesis Genes

The expression patterns of eight genes known to function in insulin-synthesis were compared with the expression patterns of novel genes with unknown function to determine whether a specified coexpression probability threshold was met. The significance of gene coexpression was evaluated using a probability method to measure a due-to-chance probability of the coexpression. The known genes were lipase, colipase, insulin, regenerating family genes, glucagon, and human islet amyloid polypeptide.

The significance of coexpression was evaluated using the Fisher exact test with probability of the coexpression set to less than 0.001, more preferably to less than 0.00001. A Bonferroni correction (Rice (1988) *Mathematical Statistics and Data Analysis*, Duxbury Press, Pacific Grove Calif. p. 384) was applied to correct statistical results of one gene being compared with multiple other genes. Through this comparison, AQP8V was identified as having a high coexpression probability with the known insulin synthesis genes. U.S. Ser. No. 09/226,994 filed Jan. 7, 1999, is hereby incorporated by reference herein.

V Extension of cDNA Sequences

The cDNAs were extended using the cDNA clone and oligonucleotide primers. One primer was synthesized to initiate 5' extension of the known fragment, and the other, to initiate 3' extension of the known fragment. The initial primers were designed using OLIGO 4.06 software (National Biosciences), to be about 22 to 30 nucleotides in length, to have a GC content of about 50% or more, and to anneal to the target sequence at temperatures of about 68C to about 72 C. Any stretch of nucleotides that would result in hairpin structures and primer-primer dimerizations was avoided.

Selected cDNA libraries were used as templates to extend the sequence. If more than one extension was necessary, additional or nested sets of primers were designed. Preferred libraries have been size-selected to include larger cDNAs and random primed to contain more sequences with 5' or upstream regions of genes. Genomic libraries are used to obtain regulatory elements, especially extension into the 5' promoter binding region.

High fidelity amplification was obtained by PCR using methods such as that taught in U.S. Pat. No. 5,932,451. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair PCI A and PCI B (Incyte Genomics): Step 1: 94C, three min; Step 2: 94C, 15 sec; Step 3: 60C, one min; Step 4: 68C, two min; Step 5: Steps 2, 3, and 4 repeated 20 times; Step 6: 68C, five min; Step 7: storage at 4 C. In the alternative, the parameters for primer pair T7 and SK+ (Stratagene) were as follows: Step 1: 94 C, three min; Step 2: 94C 15 sec; Step 3: 57C one min; Step 4: 68C two min; Step 5: Steps 2, 3, and 4 repeated 20 times; Step 6: 68C five min; Step 7: storage at 4 C.

The concentration of DNA in each well was determined by dispensing 100 µl PICOGREEN quantitation reagent (0.25% reagent in 1x TE, v/v; Molecular Probes) and 0.5 µl of undiluted PCR product into each well of an opaque fluorimeter plate (Coming, Acton Mass.) and allowing the DNA to bind to the reagent. The plate was scanned in a Fluoroskan II (Labsystems Oy) to measure the fluorescence of the sample and to quantify the concentration of DNA. A 5 µl to 10 µl aliquot of the reaction mixture was analyzed by electrophoresis on a 1% agarose mini-gel to determnine which reactions were successful in extending the sequence.

The extended clones were desalted, concentrated, transferred to 384-well plates, digested with CviJI cholera virus endonuclease (Molecular Biology Research, Madison Wis.), and sonicated or sheared prior to religation into pUC 18 vector (APB). For shotgun sequences, the digested nucleotide sequences were separated on low concentration (0.6 to 0.8%) agarose gels, fragments were excised, and the agar was digested with AGARACE enzyme (Promega). Extended clones were religated using T4 DNA ligase (New England Biolabs) into pUC 18 vector (APB), treated with Pfu DNA polymerase (Stratagene) to fill-in restriction site overhangs, and transfected into E. coli competent cells. Transformed cells were selected on antibiotic-containing media, and individual colonies were picked and cultured overnight at 37C in 384-well plates in LBI2x carbenicillin liquid media.

The cells were lysed, and DNA was amplified using primers, Taq DNA polymerase (APB) and Pfu DNA polymerase (Stratagene) with the following parameters: Step 1: 94C, three min; Step 2: 94C, 15 sec; Step 3: 60C, one min; Step 4: 72C, two min; Step 5: steps 2, 3, and 4 repeated 29 times; Step 6: 72C, five min; Step 7: storage at 4C. DNA was quantified using PICOGREEN quantitative reagent (Molecular Probes) as described above. Samples with low DNA recoveries were reamplified using the conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (APB) or the ABI PRISM BIGDYE terminator cycle sequencing kit (PE Biosystems).

VI Homology Searching of cDNA Clones and Their Deduced Proteins

The cDNAs of the Sequence Listing or their deduced amino acid sequences were used to query databases such as GenBank, SwissProt, BLOCKS, and the like. These databases that contain previously identified and annotated sequences or domains were searched using BLAST or BLAST 2 (Altschul et al. supra; Altschul, supra) to produce alignments and to determine which sequences were exact matches or homologs. The alignments were to sequences of prokaryotic (bacterial) or eukaryotic (animal, fungal, or plant) origin. Alternatively, algorithms such as the one described in Smith and Smith (1992, Protein Engineering 5:35–51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin (supra), BLAST matches between a query sequence and a database sequence were evaluated statistically and only reported when they satisfied the threshold of $10^{-25}$ for nucleotides and $10^{-14}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the electronic stringency for an exact match was set at 70, and the conservative lower limit for an exact match was set at approximately 40 (with 1–2% error due to uncalled bases).

The BLAST software suite, freely available sequence comparison algorithms (NCBI, Bethesda Md.; http://www.ncbi.nlm.nih.gov/gorf/bl2.html) includes various sequence analysis programs including "blastn", that is used to align a known nucleic acid molecules, BLAST 2 that is used for direct pairwise comparison of either nucleic or amino acid molecules. BLAST programs are commonly used with gap and other parameters set to default settings, e.g.: Matrix: BLOSUM62; Reward for match: 1; Penalty for mismatch: –2; Open Gap: 5 and Extension Gap: 2 penalties; Gap x drop-off: 50; Expect: 10; Word Size: 11; and Filter: on. Identity is measured over the entire length of a sequence or some smaller portion thereof. Brenner et al. (1998; Proc Natl Acad Sci 95:6073–6078, incorporated herein by reference) analyzed the BLAST for its ability to identify structural homologs by sequence identity and found 30% identity is a reliable threshold for sequence alignments of at least 150 residues and 40%, for alignments of at least 70 residues.

The mammalian cDNAs of this application were compared with assembled consensus sequences or templates found in the LIFESEQ GOLD database. Component sequences from cDNA, extension, full length, and shotgun sequencing projects were subjected to PHRED analysis and assigned a quality score. All sequences with an acceptable quality score were subjected to various pre-processing and editing pathways to remove low quality 3' ends, vector and linker sequences, polyA tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another and those having local similarity of at least 82% were combined and reassembled. Bins having templates with less than 95% local identity were split. Templates were subjected to analysis by STITCHER/EXON MAPPER algorithms that analyze the probabilities of the presence of splice variants, alternatively spliced exons, splice junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homolog match as having an E-value (or probability score) of $\leq 1\times 10^{-8}$. The templates were also subjected to frameshift FASTx against GENPEPT, and homolog match was defined as having an E-value of $\leq 1\times 10^{-8}$. Template analysis and assembly was described in U.S. Ser. No. 09/276,534, filed Mar. 25, 1999.

Following assembly, templates were subjected to BLAST, motif, and other functional analyses and categorized in protein hierarchies using methods described in U.S. Ser. No. 08/812,290 and U.S. Ser. No. 08/811,758, both filed Mar. 6, 1997; in U.S. Ser. No. 08/947,845, filed Oct. 9, 1997; and in U.S. Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis Mo.; http:H/pfam.wustl.edu/).

The cDNA was further analyzed using MACDNASIS PRO software (Hitachi Software Engineering), and LASER-GENE software (DNASTAR) and queried against public databases such as the GenBank rodent, mammalian, vertebrate, prokaryote, and eukaryote databases, SwissProt, BLOCKS, PRINTS, PFAM, and Prosite.

VII Chromosome Mapping

Radiation hybrid and genetic mapping data available from public resources such as the Stanford Human Genome Center (SHGC), Whitehead Institute for Genome Research (WIGR), and Généthon are used to determine if any of the cDNAs presented in the Sequence Listing have been mapped. Any of the fragments of the cDNA encoding AQP8V that have been mapped result in the assignment of all related regulatory and coding sequences mapping to the same location. The genetic map locations are described as ranges, or intervals, of human chromosomes. The map position of an interval, in cM (which is roughly equivalent to 1 megabase of human DNA), is measured relative to the terminus of the chromosomal p-arm.

VIII Hybridization Technologies and Analyses
Immobilization of cDNAs on a Substrate The cDNAs are applied to a substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37C for 16 hr. The membrane is removed from the agar and consecutively placed colony side up in 10% SDS, denaturing solution (1.5 M NaCl, 0.5 M NaOH ), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 µg. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807,522. Polymer-coated slides are prepared by cleaning glass microscope slides (Corning, Acton MA) by ultrasound in 0.1% SDS and acetone, etching in 4% hydrofluoric acid (VWR Scientific Products, West Chester Pa.), coating with 0.05% aminopropyl silane (Sigma Aldrich) in 95% ethanol, and curing in a 110C oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford MA) for 30 min at 60C; then the arrays are washed in 0.2% SDS and rinsed in distilled water as before.

Probe Preparation for Membrane Hybridization

Hybridization probes derived from the cDNAs of the Sequence Listing are employed for screening cDNAs, mRNAs, or genomic DNA in membrane-based hybridizations. Probes are prepared by diluting the cDNAs to a concentration of 40–50 ng in 45 µl TE buffer, denaturing by heating to 100C for five min, and briefly centrifuging. The denatured cDNA is then added to a REDIPRIME tube (APB), gently mixed until blue color is evenly distributed, and briefly centrifuged. Five µl of [$^{32}$P]dCTP is added to the tube, and the contents are incubated at 37C for 10 min. The labeling reaction is stopped by adding 5 µl of 0.2M EDTA, and probe is purified from unincorporated nucleotides using a PROBEQUANT G-50 microcolumn (APB). The purified probe is heated to 100C for five min, snap cooled for two min on ice, and used in membrane-based hybridizations as described below.

Probe Preparation for Polymer Coated Slide Hybridization

Hybridization probes derived from mRNA isolated from samples are employed for screening cDNAs of the Sequence Listing in array-based hybridizations. Probe is prepared using the GEMbright kit (Incyte Genomics) by diluting mRNA to a concentration of 200 ng in 9 µl TE buffer and adding 5 µl 5× buffer, 1 µl 01 M DTT, 3 µl Cy3 or Cy5 labeling mix, 1 µl RNase inhibitor, 1 µl reverse transcriptase, and 5 µl 1× yeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37C for two hr. The reaction mixture is then incubated for 20 min at 85C and probes are purified using two successive CHROMA SPIN+TE 30 columns (Clontech, Palo Alto Calif.). Purified probe is ethanol precipitated by diluting probe to 90 µl in DEPC-treated water, adding 2 µl 1mg/ml glycogen, 60 µl 5

M sodium acetate, and 300 µl 100% ethanol. The probe is centrifuged for 20 min at 20,800×g, and the pellet is resuspended in 12 µl resuspension buffer, heated to 65C for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1× high phosphate buffer (0.5 M NaCl, 0.1 M Na$_2$HPO$_4$, 5 mM EDTA, pH 7) at 55C for two hr. The probe, diluted in 15 ml fresh hybridization solution, is then added to the membrane. The membrane is hybridized with the probe at 55C for 16 hr. Following hybridization, the membrane is washed for 15 min at 25C in 1 mM Tris,(pH 8.0), 1% Sarkosyl, and four times for 15 min each at 25C in 1 mM Tris (pH 8.0). To detect hybridization complexes, XOMAT-AR film (Eastman Kodak, Rochester N.Y.) is exposed to the membrane overnight at −70C developed, and examined visually.

Polymer Coated Slide-based Hybridization

Probe is heated to 65C for five min, centrifuged five min at 9400 rpm in a 5415C microcentrifuge (Eppendorf Scientific, Westbury N.Y.), and then 18 µl is aliquoted onto the array surface and covered with a coverslip. The arrays are transferred to a waterproof chamber having a cavity just slightly larger than a microscope slide. The chamber is kept at 100% humidity internally by the addition of 140 µl of 5×SSC in a corner of the chamber. The chamber containing the arrays is incubated for about 6.5 hr at 60C. The arrays are washed for 10 min at 45C in 1×SSC, 0.1% SDS, and three times for 10 min each at 45C in 0.1×SSC, and dried.

Hybridization reactions are performed in absolute or differential hybridization formats. In the absolute hybridization format, probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to substantially equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20X microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (AID) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

IX Electronic Analysis

BLAST was used to search for identical or related molecules in the GenBank or LIFESEQ databases (Incyte Genomics). The product score for human and rat sequences was calculated as follows: the BLAST score is multiplied by the % nucleotide identity and the product is divided by (5 times the length of the shorter of the two sequences), such that a 100% alignment over the length of the shorter sequence gives a product score of 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

Electronic northern analysis was performed at a product score of 70 and is shown in FIG. 3. All sequences and cDNA libraries in the LIFESEQ database were categorized by system, organ/tissue and cell type. The categories included cardiovascular system, connective tissue, digestive system, embryonic structures, endocrine system, exocrine glands, female and male genitalia, germ cells, hemic/immune system, liver, musculoskeletal system, nervous system, pancreas, respiratory system, sense organs, skin, stomatognathic system, unclassified/mixed, and the urinary tract. For each category, the number of libraries in which the sequence was expressed were counted and shown over the total number of libraries in that category. In a non-normalized library, expression levels of two or more are significant.

X Complementary Molecules

Molecules complementary to the cDNA, from about 5 (PNA) to about 5000 bp (complement of a cDNA insert), are used to detect or inhibit gene expression. These molecules are selected using OLIGO 4.06 software (National Biosciences). Detection is described in Example VII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in "triple helix"

base pairing to compromise the ability of the double helix to open sufficiently for the binding of polymerases, transcription factors, or regulatory molecules. To inhibit translation, a complementary molecule is designed to prevent ribosomal binding to the mRNA encoding the mammalian protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if appropriate elements for inducing vector replication are used in the transformation/expression system.

Stable transformation of appropriate dividing cells with a vector encoding the complementary molecule produce a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the cDNA encoding the mammalian protein.

XI Expression of AQP8V

Expression and purification of the mammalian protein are achieved using either a mammalian cell expression system or an insect cell expression system. The pUB6/V5-His vector system (Invitrogen, Carlsbad Calif.) is used to express AQP8V in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6xHis) sequence for rapid purification on PROBOND resin (Invitrogen). Transformed cells are selected on media containing blasticidin.

*Spodoptera fruliwerda* (Sf9) insect cells are infected with recombinant *Autographica californica* nuclear polyhedrosis virus (baculovirus). The polyhedrin gene is replaced with the mammalian cDNA by homologous recombination and the polyhedrin promoter drives cDNA transcription. The protein is synthesized as a fusion protein with 6xhis which enables purification as described above. Purified protein is used in the following activity and to make antibodies.

XII Production of Antibodies

AQP8V is purified using polyacrylamide gel electrophoresis and used to immunize mice or rabbits. Antibodies are produced using the protocols below. Alternatively, the amino acid sequence of AQP8V is analyzed using LASER-GENE software (DNASTAR) to determine regions of high antigenicity and an antigenic epitope of about 15 residues in length is selected, synthesized, and used to raise antibodies. Oligopeptides are produced using an ABI 431A peptide synthesizer (PE Biosystems) using Fmoc-chemistry and coupled to KLH (Sigma-Aldrich) by reaction with N-maleimidobenzoyl-N-hydroxysuccinimide ester to increase antigenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and to prepare disease and control standards based on the amount of complex formation against which a subject sample is compared.

XIII Purification of Naturally Occurring Protein Using Specific Antibodies

Naturally occurring or recombinant protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XIV Screening Molecules for Specific Binding with the cDNA or Protein

The cDNA, or fragments thereof, or the protein, or portions thereof, are labeled with $^{32}$P-dCTP, Cy3-dCTP, or Cy5-dCTP (APB), or with BIODIPY or FTC (Molecular Probes, Eugene Orerg.), respectively. Libraries of candidate molecules or compounds previously arranged on a substrate are incubated in the presence of labeled cDNA or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XV Two-Hybrid Screen

A yeast two-hybrid system, MATCHMAKER LexA Two-Hybrid system (Clontech Laboratories, Palo Alto Calif.), is used to screen for peptides that bind the mammalian protein of the invention. A cDNA encoding the protein is inserted into the multiple cloning site of a pLexA vector, ligated, and transformed into *E. coli*. cDNA, prepared from mRNA, is inserted into the multiple cloning site of a pB42AD vector, ligated, and transformed into *E. coli* to construct a cDNA library. The pLexA plasmid and pB42AD-cDNA library constructs are isolated from *E. coli* and used in a 2:1 ratio to co-transform competent yeast EGY48[p8op-lacZ] cells using a polyethylene glycolllithium acetate protocol. Transformed yeast cells are plated on synthetic dropout (SD) media lacking histidine (-His), tryptophan (-Trp), and uracil (-Ura), and incubated at 30C until the colonies have grown up and are counted. The colonies are pooled in a minimal volume of 1xTE (pH 7.5), replated on SD/-His/-Leu/-Trp/-Ura media supplemented with 2% galactose (Gal), 1% raffinose (Raf), and 80 mg/ml 5-bromo-4chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of β-galactosidase from the p8op-lacZ reporter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30C. A sample of the culture is plated on SD/-Trp/-Ura media and incubated at 30C until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42-cDNA plasmid, which contains a cDNA encoding a protein that physically interacts with the mammalian protein, is isolated from the yeast cells and characterized.

XVI AQP8V Activity Assay

AQP8 activity is determined in a ligand-binding assay using candidate ligand molecules in the presence of $^{125}$I-labeled AQP8V. AQP8V is labeled with $^{125}$I Bolton-Hunter reagent (Bolton and Hunter (1973) Biochem J 133:529–539). Candidate ligand molecules, previously arrayed in the wells of a multi-well plate, are incubated with the labeled AQP8V, washed, and any wells with labeled AQP8V complex are assayed. Data obtained using different concentrations of AQP8V are used to calculate values for the number, affinity, and association of AQP8V with the candidate molecules.

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

What is claimed is:

1. An isolated cDNA encoding a protein having the amino acid sequence of SEQ ID NO:1 or an oligopeptide having antigenic activity extending from residue 171 to residue 179 of SEQ ID NO:1.

2. The composition comprising the cDNA or the complement of the cDNA of claim 1.

3. A substrate comprising the cDNA or the complement of the cDNA of claim 1.

4. A probe comprising the cDNA or the complement of the cDNA of claim 1.

5. A method for using a cDNA to detect the differential expression of a nucleic acid in a sample comprising:
   a) hybridizing the probe of claim 4 to the nucleic acids, thereby forming hybridization complexes; and
   b) comparing hybridization complex formation with a standard, wherein the comparison indicates the differential expression of the cDNA in the sample.

6. The method of claim 5 further comprising amplifying the nucleic acids of the sample prior to hybridization.

7. The method of claim 5 wherein detection of differential expression of the cDNA is diagnostic of type I diabetes.

8. A vector comprising the cDNA of claim 1.

9. A host cell comprising the vector of claim 8.

10. A method for producing a protein, the method comprising:
    a) culturing the host cell of claim 9 under conditions for protein expression; and
    b) recovering the protein from the host cell culture.

11. A method of using a cDNA to screen a plurality of molecules or compounds, the method comprising:
    a) combining the cDNA of claim 1 with a plurality of molecules or compounds under conditions to allow specific binding; and
    b) detecting specific binding, thereby identifying a molecule or compound which specifically binds the cDNA.

12. The method of claim 11 wherein the plurality of molecules or compounds is selected from DNA molecules, RNA molecules, peptide nucleic acids, peptides, transcription factors, and regulatory proteins.

13. An isolated cDNA comprising a polynucleotide selected from:
    a) a polynucleotide having the nucleic acid sequence of SEQ ID NO:2;
    b) a polynucleotide extending from nucleotide 1 to nucleotide 200 of SEQ ID NO:2;
    c) an oligonucleotide extending from nucleotide 90 to nucleotide 105 of SEQ ID NO:2; and
    d) a complement of the polynucleotide of a)–c).

* * * * *

UNITED STATES PATENT AND TRADEMARK OFFICE
CERTIFICATE OF CORRECTION

PATENT NO.    : 6,566,066 B1
DATED         : May 20, 2003
INVENTOR(S)   : Walker et al.

It is certified that error appears in the above-identified patent and that said Letters Patent is hereby corrected as shown below:

<u>Column 41,</u>
Lines 38-39, please replace "The composition comprising the cDNA or the complement of the cDNA of claim 1." with
-- The composition comprising the cDNA or the complement of the cDNA of claim 1 and a reporter molecule. --

Signed and Sealed this

Second Day of December, 2003

JAMES E. ROGAN
*Director of the United States Patent and Trademark Office*